United States Patent
Owens et al.

(10) Patent No.: US 8,263,101 B2
(45) Date of Patent: Sep. 11, 2012

(54) PASSIVE METHODS FOR ANTI-MICROBIAL BIOLOGICAL MESHES

(75) Inventors: Rick T. Owens, Stewartsville, NJ (US); Mike Liu, Hillsborough, NJ (US); Yong Mao, Basking Ridge, NJ (US)

(73) Assignee: Lifecell Corporation, Branchburg, NJ (US)

( * ) Notice: Subject to any disclaimer, the term of this patent is extended or adjusted under 35 U.S.C. 154(b) by 0 days.

(21) Appl. No.: 13/217,566

(22) Filed: Aug. 25, 2011

(65) Prior Publication Data

US 2012/0053322 A1    Mar. 1, 2012

Related U.S. Application Data

(60) Provisional application No. 61/377,182, filed on Aug. 26, 2010.

(51) Int. Cl.
*A61F 13/00* (2006.01)
*A61F 2/00* (2006.01)
(52) U.S. Cl. ........................ 424/422; 424/423
(58) Field of Classification Search .................. 530/356; 424/422, 424
See application file for complete search history.

(56) References Cited

U.S. PATENT DOCUMENTS

| | | | |
|---|---|---|---|
| 4,599,226 | A | 7/1986 | Fox, Jr. et al. |
| 5,336,616 | A | 8/1994 | Livesey et al. |
| 5,364,756 | A | 11/1994 | Livesey et al. |
| 6,969,523 | B1 | 11/2005 | Mattern et al. |
| 8,067,149 | B2 | 11/2011 | Livesey et al. |
| 2003/0143207 | A1 | 7/2003 | Livesey et al. |
| 2005/0028228 | A1 | 2/2005 | McQuillan et al. |
| 2007/0248575 | A1 | 10/2007 | Connor et al. |
| 2008/0027542 | A1 | 1/2008 | McQuillan et al. |
| 2009/0035342 | A1 | 2/2009 | Karandikar et al. |
| 2009/0311298 | A1 | 12/2009 | Nixon et al. |

FOREIGN PATENT DOCUMENTS

| | | |
|---|---|---|
| WO | WO 2007/048099 | 4/2007 |
| WO | WO 2007/106581 | 9/2007 |
| WO | WO 2009/105760 | 8/2009 |

OTHER PUBLICATIONS

International Search Report and Written Opinion for PCT/US2011/049062 mailed Nov. 3, 2011, from the International Search Authority of the European Patent Office.

*Primary Examiner* — Maryam Monshipouri
(74) *Attorney, Agent, or Firm* — Finnegan, Henderson, Farabow, Garrett & Dunner, LLP

(57) ABSTRACT

Tissue matrices having anti-microbial properties are provided. In certain embodiments, the tissue matrices include cationic anti-microbial agents that form a stable bond with the tissue matrices without adversely affecting the biologic properties of the tissue matrices.

27 Claims, 5 Drawing Sheets

PASSIVE METHODS FOR ANTI-MICROBIAL BIOLOGICAL MESHES

This application claims priority under 35 U.S.C. §119 to U.S. Provisional Patent Application No., 61/377,182, which was filed on Aug. 26, 2010, and is herein incorporated by reference.

The present disclosure relates to tissue matrices, and more particularly, to methods of preparing tissue matrices that incorporate anti-microbial agents and tissue matrices prepared according to those methods.

Various tissue-derived matrices are used to regenerate, repair, or otherwise treat diseased or damaged tissues and organs. Such matrices can include intact tissue grafts and/or acellular or reconstituted acellular tissues (e.g., acellular tissue matrices from skin, intestine, or other tissues, with or without cell seeding). As with many implanted foreign bodies, infection can occur following the use of such materials in surgical applications.

Production of tissue matrices with increased anti-microbial activity may reduce the rate of graft infection and increase the likelihood of success after surgery. Accordingly, methods for producing biological materials by binding of anti-microbial agents to a tissue matrix are provided. In addition, tissue matrices produced by such methods are also provided.

According to certain embodiments, a method for preparing a modified tissue matrix is provided. The method comprises selecting a collagen-based tissue matrix and contacting the tissue matrix with an aqueous solution containing a cationic anti-microbial agent, wherein the agent stably binds to the matrix by passive adsorption.

In certain embodiments, a modified tissue matrix is provided. The modified tissue matrix comprises a tissue matrix that has been prepared by selecting a collagen-based tissue matrix and contacting the matrix with an aqueous solution containing a cationic anti-microbial agent, wherein the agent is stably bound to the matrix by passive adsorption.

In certain embodiments, a modified tissue matrix is provided. The modified tissue matrix comprises a collagen-based tissue matrix and at least one cationic anti-microbial agent that is stably bound to the matrix by passive adsorption.

DESCRIPTION OF CERTAIN EXEMPLARY EMBODIMENTS

Figure 1:
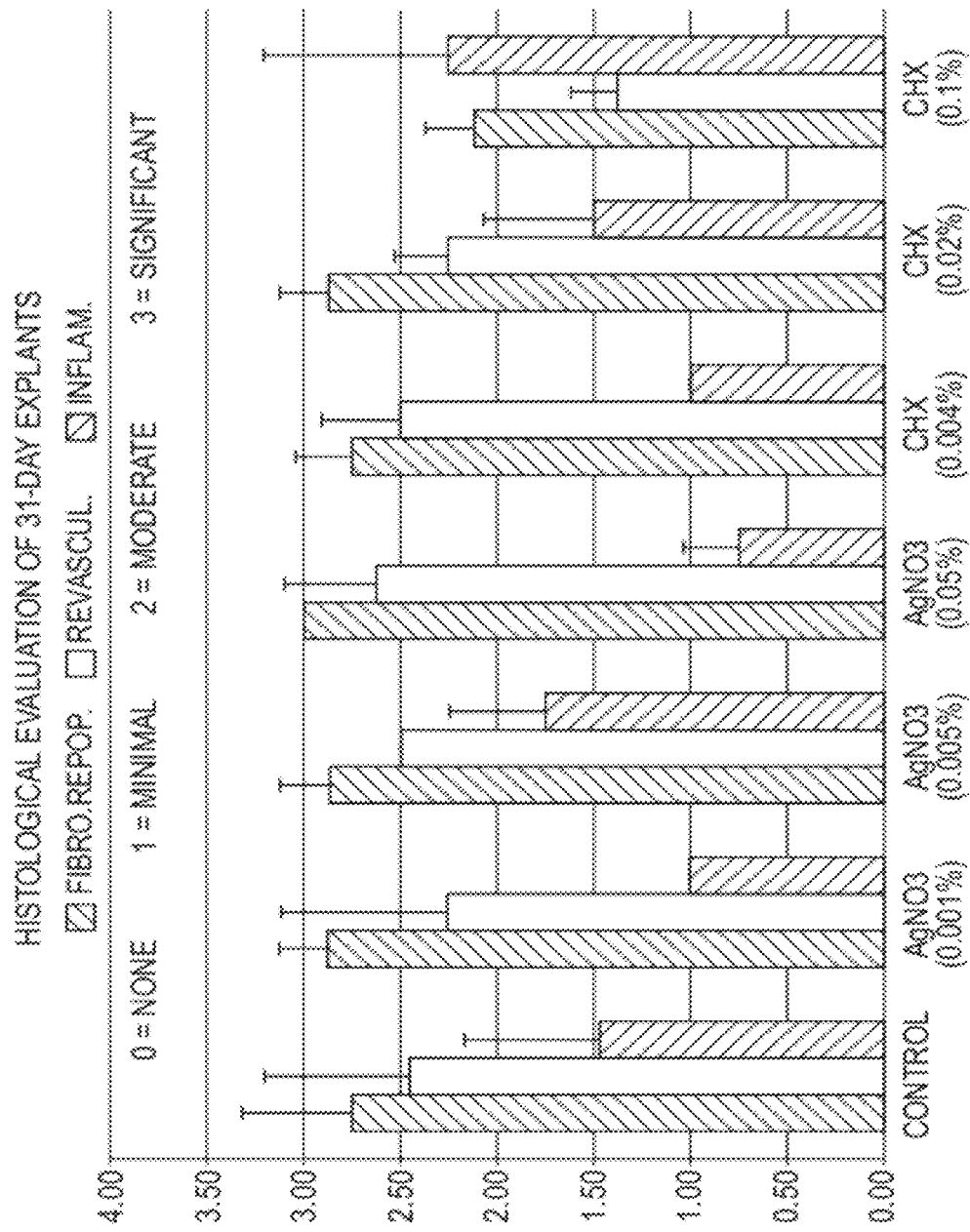
FIG. 1 is a chart comparing the in vivo tissue response of various tissue matrices, according to certain embodiments, as described in Example 1.

Reference will now be made in detail to certain exemplary embodiments according to the present disclosure, certain examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Any range described herein will be understood to include the endpoints and all values between the endpoints.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

As used herein, "tissue matrix" will refer to material derived from animal tissue that includes a collagen-containing matrix. Such tissue matrices can include intact tissues, tissues that have been partially or completely decellularized, or synthetic collagenous matrices (e.g., 3-D matrices formed from suspended or otherwise processed tissues). As described further below, suitable tissue matrices can be acellular. Any suitable tissue matrix can be used, depending on the intended implantation site, so long as the tissue stably binds anti-microbial agents, as described herein. The stability of binding of the anti-microbial agents can be determined in a number of ways. For example, one method for measuring stability is described below in Example 3, wherein the modified tissue matrices are washed in PBS at body temperature for 14 days to determine if washing in such buffers results in loss of anti-microbial properties.

Various human and animal tissue matrices can be used to produce matrices for treating patients. For example, various tissue matrices are available for regeneration, repair, augmentation, reinforcement, and/or treatment of human tissues that have been damaged or lost due to various diseases and/or structural damage (e.g., from trauma, surgery, atrophy, and/or long-term wear and degeneration) have been produced. However, such tissues are generally implanted using invasive procedures, and such procedures (e.g., including an incision, puncture, etc), can predispose a patient to infection. In addition, a foreign body, including a tissue matrix or other implantable device used in conjunction with the implant (e.g., breast implant, polymer mesh, etc.) can increase the chance of infection after surgery. Accordingly, acellular tissue matrices that reduce the chance of infection are desirable.

According to certain embodiments, a method for preparing a tissue matrix is provided. The method comprises selecting a collagen-based tissue matrix and contacting the tissue matrix with an aqueous solution containing a cationic anti-microbial agent, wherein the agent stably binds to the matrix by passive adsorption. This method eliminates the need to chemically modify the anti-microbial or the tissue matrix, thereby ensuring complete functionality of the respective components. In certain embodiments, a tissue matrix is provided. The matrix comprises a tissue matrix that has been prepared by selecting a collagen-based tissue matrix and contacting the matrix in an aqueous solution containing a cationic anti-microbial agent, wherein the agent is stably bound to the matrix by passive adsorption. In certain embodiments, a tissue matrix is provided. The matrix comprises a collagen-based tissue matrix and at least one cationic anti-microbial agent that is stably bound to the matrix by passive adsorption.

In various embodiments, the solution used to apply the cationic anti-microbial agent can include a variety of different aqueous solutions. For example, in some embodiments, the aqueous solution used is non-denaturing. Non-denaturing conditions allow the anti-microbial agents to retain their cationic properties, which permits binding by passive adsorption. The solution must allow the antimicrobial agent to present a positive charge which is necessary for binding to the tissue. The solution must also be compatible with the tissue matrix and not induce permanent or irreversible damage. In one embodiment, the non-denaturing aqueous solution is water. In various embodiments, the solution comprises, for example, isotonic saline, PBS, HEPES, or other suitable buffers.

Any suitable cationic antimicrobial agent can be used with the processes and tissue matrices of the present disclosure. In certain embodiments, the anti-microbial agent includes at least one of benzethonium chloride, chlorhexidine, benzalkonium chloride, and silver nitrate. In other embodiments, the anti-microbial compound includes poly-hexa-methylene biguanide hydrochloride. In some embodiments, suitable anti-microbial compounds also include cationic peptides such as nisin, cathelicidin, and abaecin. Additional suitable anti-microbial compounds include quaternary ammonium compounds such as methylbenzethonium chloride, cetalkonium chloride, dofanium chloride, tetraethylammonium bromide, didecyldimethylammonium chloride, and domiphen bromide. In some embodiments, combinations of different anti-microbial agents can be used. Examples of anti-microbial combinations include silver and chlorhexidine as well as chlorhexidine with various quaternary ammonium compounds.

The amount of cationic anti-microbial agent in the non-denaturing aqueous solution can be prepared at various concentrations. The specific concentration may depend on a variety of factors. For example, for some applications, the potential risk of infection may be higher than others, and higher concentrations of anti-microbials may be used. In other cases, too much anti-microbial may have toxic or otherwise adverse effects on tissues, and lower concentrations may be selected.

In certain embodiments, the concentration of benzethonium chloride in water or HEPES can range from 0.025% to 1.0% w/v or from 0.01% to 1.0% w/v. In certain embodiments, the concentration of chlorhexidine in water or HEPES can range from 0.002% to 0.2% w/v. In some embodiments, the concentration of silver nitrate in water or HEPES can range from 0.0005% to 0.1% w/v. In some embodiments, the concentration of benzethonium chloride is 0.05%, 0.25%, or 0.5% w/v, or at least 0.05%, 0.25%, or 0.5% w/. In some embodiments, the concentration of chlorhexidine is 0.004%, 0.02%, or 0.1% w/v, or at least 0.004%, 0.02%, or 0.1% w/v. In some embodiments, the concentration of silver nitrate is 0.001%, 0.005%, or 0.05% w/v, or at least 0.001%, 0.005%, or 0.05% w/v. In other embodiments, the concentration of benzalkonium chloride is 0.02%, 0.1%, or 0.5% w/v, or at least 0.02%, 0.1%, or 0.5% w/v. In one aspect, the concentrations disclosed are effective at least over 7 days. In another aspect, the concentrations are effective at least over 14 days.

In one embodiment, cationic anti-microbial agents such as chlorhexidine, quaternary ammonium compounds, chitosan, or silver ions are dissolved in water or an appropriate solvent at a suitable concentration. The acellular tissue matrix is then placed in the anti-microbial solution and incubated for a time and temperature sufficient to allow binding of a desired amount of antimicrobial. For example, a typical incubation time for antimicrobials dissolved in HEPES or water is 4 hours at room temperature. After incubation, unbound antimicrobial compounds are then removed by washing in a buffer such as HEPES.

Processing acellular tissue matrices to improve the anti-microbial properties of the matrices can adversely affect the biologic properties of such matrices. For example, chemical cross-linking can be used to bind the anti-microbial agent to the matrix, but excessive cross-linking can alter the biologic properties of the tissue, thereby preventing the desired tissue response when implanted (e.g., regeneration, remodeling, reinforcement, repair, etc. depending on the specific use). Excessive cross-linking may also adversely affect the anti-microbial activity of the agent used. In addition, chemical cross-linking agents may be harmful to patients once implanted in the body. Accordingly, in some embodiments, the methods of the present disclosure allow production of acellular tissue matrices that include anti-microbial compounds, which are stably bound to the matrices without use of chemical cross-linking. Since the collagenous matrix is not significantly altered, i.e., is not cross-linked or denatured, the process does not cause unsuitable changes in the inherent regenerative tissue response of the matrix in vivo as determined by cellular infiltration, revascularization, and inflammation of treated tissues. Cross-linking or denaturing of proteins can be measured using a number of processes such as differential scanning calorimetry (DSC) or collagenase digestion assays, which can show changes due to cross-linking, denaturing, or other protein alterations.

In addition, the binding of the anti-microbial compound to the tissue matrix by passive adsorption does not modify the anti-microbial agent. Other means of binding, such as cross-linking, may result in modifications to the anti-microbial agent, and the use of denaturing conditions may also lead to modifications of the anti-microbial agent. These modifications may lead to undesired consequences, such as a loss of effectiveness. Because chemical cross-linking is not needed to bind the anti-microbial compound to the matrices, the anti-microbial compound is not unacceptably modified by the binding process, and anti-microbial activity is preserved.

As previously noted, implantable tissue matrices may be implanted in or on the body during surgery or using other somewhat invasive procedures. It is beneficial that any anti-microbial properties possessed by these matrices remain active during the critical period for opportunistic infection following surgery, usually one to two weeks. In one embodiment, the anti-microbial properties resulting of the tissue matrices produced from the disclosed method are active for a significant time period after implantation in or on the body. For example, in various embodiments, the anti-microbial properties are retained for at least a week, at least two weeks, at least three weeks, or at least a month after implantation.

The disclosed method and tissue matrices can be used in conjunction with a variety of other tissue processing steps. For example, implantable tissue matrices are typically treated to produce aseptic or sterile materials. Accordingly, in various embodiments, the tissue matrices can be processed to bind anti-microbial compounds before and/or after performance of other sterilization processes designed to reduce or eliminate tissue pathogens. As used herein, a "sterilization process" can include any process that reduces bioburden in a sample, but need not render the sample absolutely sterile.

Certain exemplary processes include, but are not limited to, a gamma irradiation process, an e-beam irradiation process, a supercritical carbon dioxide sterilization process, and a peracetic acid treatment process. Suitable sterilization processes include, but are not limited to, those described in, for example, U.S. patent Publication No. 2006/0073592A1, to Sun et al.; U.S. Pat. No. 5,460,962 to Kemp; U.S. Patent Publication No. 2008/0171092A1, to Cook et al. Application of the anti-microbial agent can occur before or after the sterilization process. In some embodiments, the sterilization process can be a terminal sterilization process that is performed just before or after packaging a tissue sample.

In certain embodiments, the anti-microbial process is applied before a terminal sterilization process using any suitable terminal sterilization process. In some embodiments, terminal sterilization of the tissue matrix may include the use of radiation. In various embodiments, suitable forms of radiation include gamma radiation and X-ray radiation. In one embodiment, sterilization is performed using E-beam radiation. Further, combinations of various sterilization processes can be used.

After processing to bind anti-microbial compounds and/or perform sterilization or other processing steps, tissue matrices may be stored for some time before implantation in or on a patient. Further, in some cases, the tissue matrices may be stored in liquid medium, e.g., aqueous preservation solutions, or may be frozen and/or freeze-dried. Accordingly, whatever storage method is used, it is important that the anti-microbial composition remains stably bound during storage. In various embodiments, the tissue matrices of the present disclosure will retain anti-microbial properties for extended periods during storage in aqueous solutions. In some embodiments, the anti-microbial compound remains stably bound during storage for up to 1 month, 2 months, 3 months, 4 months, or longer.

Suitable Tissue Matrices

As noted above, the methods described herein can be used to produce products having anti-microbial properties using a variety of different tissue types, so long as the tissue includes a collagen-containing matrix to which cationic antimicrobials can stably bind. Such tissue matrices can include intact tissues, tissues that have been partially or completely decellularized, or synthetic collagenous matrices (e.g., 3-D matrices formed from suspended or otherwise processed tissues).

The tissue matrix can be produced from a range of tissue types. For example, the tissue matrix can be derived from fascia, pericardial tissue, dura, umbilical tissue, placental tissue, cardiac valve tissue, ligament tissue, tendon tissue, arterial tissue, venous tissue, neural connective tissue, urinary bladder tissue, ureter tissue, and intestinal tissue. In other embodiments, the tissue matrix comprises a dermal tissue matrix. In certain embodiments, the tissue matrix comprises porcine dermal matrix.

In certain embodiments, the tissues can include a mammalian soft tissue. For example, in certain embodiments, the tissue can include mammalian dermis. In certain embodiments, the dermis can be separated from surrounding epidermis and/or other tissues, such as subcutaneous fat. In certain embodiments, the tissue sample can include small intestine submucosa. In certain embodiments, the tissue samples can include human or non-human sources. Exemplary, suitable non-human tissue sources include, but are not limited to, pigs, sheep, goats, rabbits, monkeys, and/or other non-human mammals.

The tissue matrices can be implanted at a variety of different anatomic sites. For example, tissue matrices can be implanted around breast implants; around or replacing vascular structures; around or replacing luminal structures (e.g., ureters, nerves, lymphatic tissues, gastrointestinal structures); on or replacing heart valves, pericardium, or other cardiac structures; in or on bony or cartilaginous materials (e.g., ears, noses, articular surfaces, around dental structures, or along any short of long bone); and/or surrounding, lining, supporting, or replacing any body cavity (e.g., bladder, stomach).

Tissue matrices can be selected to provide a variety of different biological and mechanical properties. For example, an acellular tissue matrix can be selected to allow tissue ingrowth and remodeling to assist in regeneration of tissue normally found at the site where the matrix is implanted. For example, an acellular tissue matrix, when implanted on or into fascia, may be selected to allow regeneration of the fascia without excessive fibrosis or scar formation. In certain embodiments, the tissue matrix can be formed from ALLODERM® or STRATTICE™, which are human and porcine acellular dermal matrices, respectively. Alternatively, other suitable acellular tissue matrices can be used, as described further below.

In some embodiments, the collagen-based material comprises an acellular tissue matrix. In certain embodiments, these matrices can be completely decellularized to yield acellular tissue matrices to be used for patients. For example, various tissues, such as skin, intestine, bone, cartilage, nerve tissue (e.g., nerve fibers or dura), tendons, ligaments, or other tissues can be completely decellularized to produce tissue matrices useful for patients. Suitable processes for producing acellular tissue matrices are described below.

In general, the steps involved in the production of an acellular tissue matrix include harvesting the tissue from a donor (e.g., a human cadaver or animal source) and cell removal under conditions that preserve biological and structural function. In certain embodiments, the process includes chemical treatment to stabilize the tissue and avoid biochemical and structural degradation together with or before cell removal. In various embodiments, the stabilizing solution arrests and prevents osmotic, hypoxic, autolytic, and proteolytic degradation, protects against microbial contamination, and reduces mechanical damage that can occur with tissues that contain, for example, smooth muscle components (e.g., blood vessels). The stabilizing solution may contain an appropriate buffer, one or more antioxidants, one or more oncotic agents, one or more antibiotics, one or more protease inhibitors, and/or one or more smooth muscle relaxants.

The tissue is then placed in a decellularization solution to remove viable cells (e.g., epithelial cells, endothelial cells, smooth muscle cells, and fibroblasts) from the structural matrix without damaging the biological and structural integrity of the collagen matrix. The decellularization solution may contain an appropriate buffer, salt, an antibiotic, one or more detergents (e.g., TRITON X-100™, sodium deoxycholate, polyoxyethylene (20) sorbitan mono-oleate), one or more agents to prevent cross-linking, one or more protease inhibitors, and/or one or more enzymes. In some embodiments, the decellularization solution comprises 1% TRITON X-100™ in RPMI media with Gentamicin and 25 mM EDTA (ethylenediaminetetraacetic acid). In some embodiments, the tissue is incubated in the decellularization solution overnight at 37° C. with gentle shaking at 90 rpm. For example, in some embodiments, 1-3% sodium deoxycholate or 2% sodium deoxycholate is added to the decellularization solution.

After the decellularization process, the tissue sample is washed thoroughly with saline. In some exemplary embodiments, e.g., when xenogenic material is used, the decellularized tissue is then treated overnight at room temperature with a deoxyribonuclease (DNase) solution. In some embodiments, the tissue sample is treated with a DNase solution prepared in DNase buffer (20 mM HEPES (4-(2-hydroxyethyl)-1-piperazineethanesulfonic acid), 20 mM $CaCl_2$ and 20 mM $MgCl_2$). Optionally, an antibiotic solution (e.g., Gentamicin) may be added to the DNase solution. Any suitable buffer can be used as long as the buffer provides suitable DNase activity.

While an acellular tissue matrix may be made from one or more individuals of the same species as the recipient of the acellular tissue matrix graft, this is not necessarily the case. Thus, for example, an acellular tissue matrix may be made from porcine tissue and implanted in a human patient. Species that can serve as recipients of acellular tissue matrix and donors of tissues or organs for the production of the acellular tissue matrix include, without limitation, mammals, such as humans, nonhuman primates (e.g., monkeys, baboons, or chimpanzees), pigs, cows, horses, goats, sheep, dogs, cats, rabbits, guinea pigs, gerbils, hamsters, rats, or mice.

Elimination of the α-gal epitopes from the collagen-containing material may diminish the immune response against the collagen-containing material. The α-gal epitope is expressed in non-primate mammals and in New World monkeys (monkeys of South America) as well as on macromolecules such as proteoglycans of the extracellular components. U. Galili et al., J. Biol. Chem. 263: 17755 (1988). This epitope is absent in Old World primates (monkeys of Asia and Africa and apes) and humans, however. Id. Anti-gal antibodies are produced in humans and primates as a result of an immune response to α-gal epitope carbohydrate structures on gastrointestinal bacteria. U. Galili et al., Infect. Immun. 56: 1730 (1988); R. M. Hamadeh et al., J. Clin. Invest. 89: 1223 (1992).

Since non-primate mammals (e.g., pigs) produce α-gal epitopes, xenotransplantation of collagen-containing material from these mammals into primates often results in immunological activation because of primate anti-Gal antibodies binding to these epitopes on the collagen-containing material. U. Galili et al., Immunology Today 14: 480 (1993); M. Sandrin et al., Proc. Natl. Acad. Sci. USA 90: 11391 (1993); H. Good et al., Transplant. Proc. 24: 559 (1992); B. H. Collins et al., J. Immunol. 154: 5500 (1995). Furthermore, xenotransplantation results in major activation of the immune system to produce increased amounts of high affinity anti-gal antibodies. Accordingly, in some embodiments, when animals that produce α-gal epitopes are used as the tissue source, the substantial elimination of α-gal epitopes from cells and from extracellular components of the collagen-containing material, and the prevention of re-expression of cellular α-gal epitopes can diminish the immune response against the collagen-containing material associated with anti-gal antibody binding to α-gal epitopes.

To remove α-gal epitopes, after washing the tissue thoroughly with saline to remove the DNase solution, the tissue sample may be subjected to one or more enzymatic treatments to remove certain immunogenic antigens, if present in the sample. In some embodiments, the tissue sample may be treated with an α-galactosidase enzyme to eliminate α-gal epitopes if present in the tissue. In some embodiments, the tissue sample is treated with α-galactosidase at a concentration of 300 U/L prepared in 100 mM phosphate buffer at pH 6.0. In other embodiments, the concentration of α-galactosidase is increased to 400 U/L for adequate removal of the α-gal epitopes from the harvested tissue. Any suitable enzyme concentration and buffer can be used as long as sufficient removal of antigens is achieved.

Alternatively, rather than treating the tissue with enzymes, animals that have been genetically modified to lack one or more antigenic epitopes may be selected as the tissue source. For example, animals (e.g., pigs) that have been genetically engineered to lack the terminal α-galactose moiety can be selected as the tissue source. For descriptions of appropriate animals see co-pending U.S. application Ser. No. 10/896,594 and U.S. Pat. No. 6,166,288, the disclosures of which are incorporated herein by reference in their entirety. In addition, certain exemplary methods of processing tissues to produce acellular matrices with or without reduced amounts of or lacking alpha-1,3-galactose moieties, are described in Xu, Hui. et al., "A Porcine-Derived Acellular Dermal Scaffold that Supports Soft Tissue Regeneration: Removal of Terminal Galactose-α-(1,3)-Galactose and Retention of Matrix Structure," Tissue Engineering, Vol. 15, 1-13 (2009), which is incorporated by reference in its entirety.

After the acellular tissue matrix is formed, histocompatible, viable cells may optionally be seeded in the acellular tissue matrix to produce a graft that may be further remodeled by the host. In some embodiments, histocompatible viable cells may be added to the matrices by standard in vitro cell co-culturing techniques prior to transplantation, or by in vivo repopulation following transplantation. In vivo repopulation can be by the recipient's own cells migrating into the acellular tissue matrix or by infusing or injecting cells obtained from the recipient or histocompatible cells from another donor into the acellular tissue matrix in situ. Various cell types can be used, including embryonic stem cells, adult stem cells (e.g. mesenchymal stem cells), and/or neuronal cells. In various embodiments, the cells can be directly applied to the inner portion of the acellular tissue matrix just before or after implantation. In certain embodiments, the cells can be placed within the acellular tissue matrix to be implanted, and cultured prior to implantation.

Although general process parameters for production of acellular tissue matrices are described, a variety of collagen-containing acellular materials are available, and the methods of processing such materials to produce anti-microbial properties may be used with any of those materials. For example, a number of biological scaffold materials are described by Badylak et al., and the methods of the present disclosure can be used to produce matrices with anti-microbial properties using any of those materials, or any other similar materials. Badylak et al., "Extracellular Matrix as a Biological Scaffold Material: Structure and Function," *Acta Biomaterialia* (2008), doi:10.1016/j.actbio.2008.09.013.

EXAMPLE 1

Histological Evaluation of Implanted Dermal Samples

STRATTICE™ porcine acellular tissue matrix was used to produce tissue matrices having bound cationic antimicrobial agents. The STRATTICE™ tissue matrix was obtained before terminal sterilization and processed as follows.

First, anti-microbial agent solutions were prepared using chlorhexidine (CHX) or silver nitrate ($AgNO_3$). CHX solutions were prepared by dissolving 0.004%, 0.02%, or 0.1% CHX w/v in water. $AgNO_3$ solutions were prepared by dissolving 0.001%, 0.005%, or 0.05% $AgNO_3$ w/v in water. Tissue matrices were incubated in one of the above-identified solution for four hours at room temperature. Unbound anti-microbial agent was removed by washing with saline. The tissue was then packaged in foil pouches and terminally sterilized using E-beam radiation.

Two types of controls were produced. First, standard STRATTICE™ tissue matrix was obtained from LifeCell Corporation and was used as an unprocessed control. Second, control samples were produced by incubation of the tissue matrix in water alone, i.e., with no anti-microbial agent present.

The processed and sterilized tissue matrices were cut into 1 $cm^2$ pieces and were implanted subdermally on the dorsal aspect of immune-competent rats. Explants were collected and washed with PBS at both 31 and 42 days. The explants were fixed in 10% formalin, and the fixed tissues were embedded in paraffin. Sections of tissue matrix samples were stained with hematoxylin and eosin (H&E) using standard procedures. D. C. Sheenan and B. B. Hrapchack, Theory and Practice of Histotechnology, 2nd edition, Columbus, Ohio, Battelle Press (1987).

31-day H&E stained histology slides were blindly evaluated by a histopathologist for fibroblast repopulation, revascularization, and inflammation. These parameters were scored using a scale of 0, 1, 2, or 3 (0=none, 1=minimal, 2=moderate, 3=significant). Fibroblast repopulation and revascularization are considered to be indicative of the regenerative capabilities of acellular tissue matrices. Therefore, it is desirable that any means of binding an anti-microbial agent to an acellular tissue matrix not interfere with these processes. In addition, it is generally desirable to preserve the regenerative tissue response of acellular tissue matrices without causing significant inflammation.

The histopathology analysis of 31-day day explants is summarized in FIG. 1. All acellular tissue matrices treated with silver nitrate showed fibroblast repopulation and revascularization comparable to that of the control. Samples treated with silver nitrate also did not result in significant inflammation when compared to the control. Similarly, acellular tissue matrices treated with 0.004% and 0.02% chlorhexidine showed fibroblast repopulation and revascularization comparable to that of the control without significant inflammation.

Figure 2A:
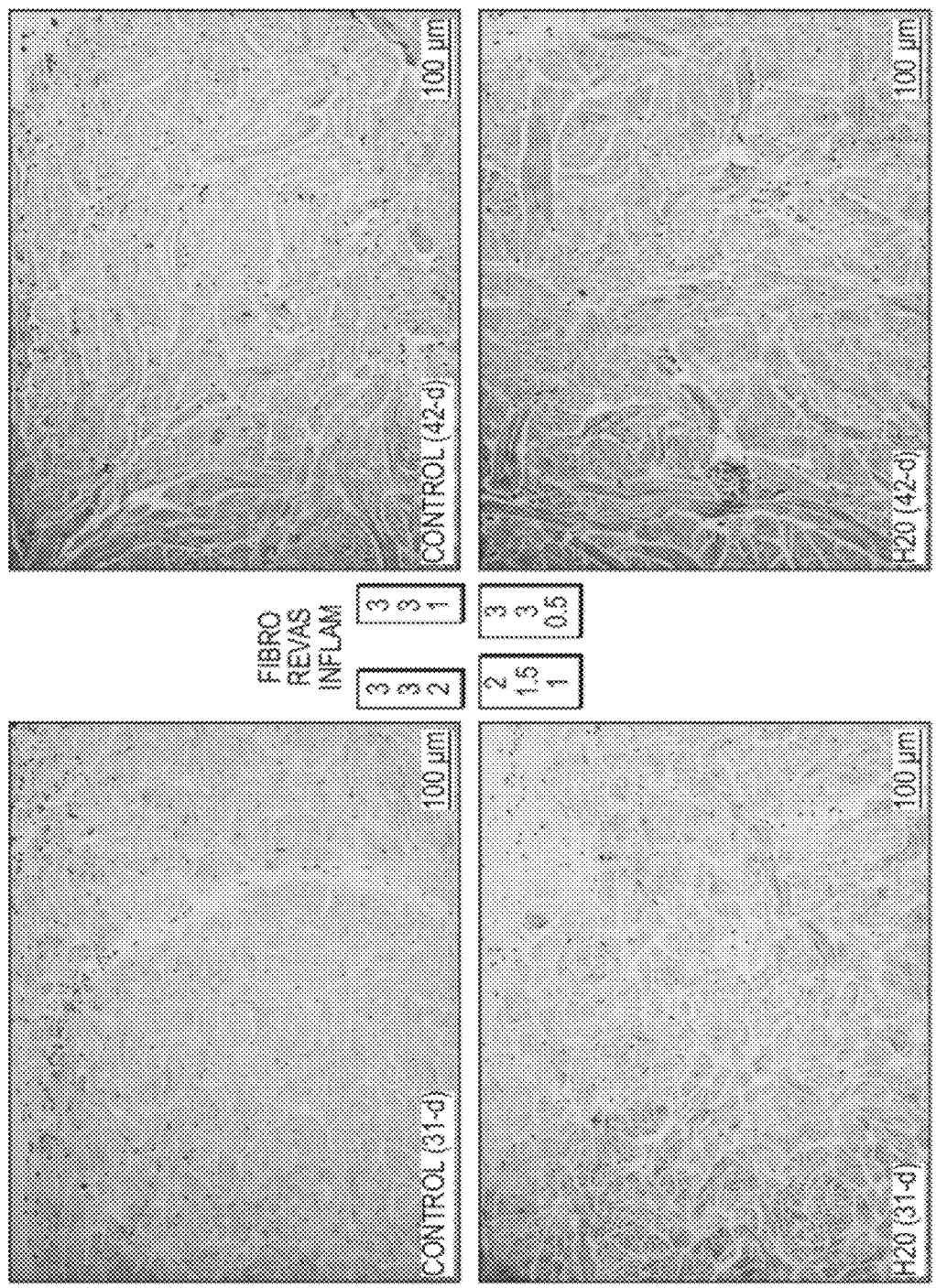
FIGS. 2A and 2B are histological sections of various tissue matrices after implantation in an animal, according to certain embodiments, as described in Example 1.

Photographs were also taken of H&E stained 31-day and 42-day sub-dermal explants under 400× magnification using a microscope. FIG. 2A shows H&E stained 31-day and 42 day sub-dermal explants prepared from control, untreated STRATTICE™ and water-treated controls. The scores of fibroblast repopulation (Fibro), revascularization (Revas) and inflammation (Inflam) are indicated near each image. After 31 days, the both untreated and water-treated controls showed significant fibroblast repopulation (Fibro=3), significant revascularization (Reva=3), and moderate inflammation (Inflam=2).

Figure 2B:
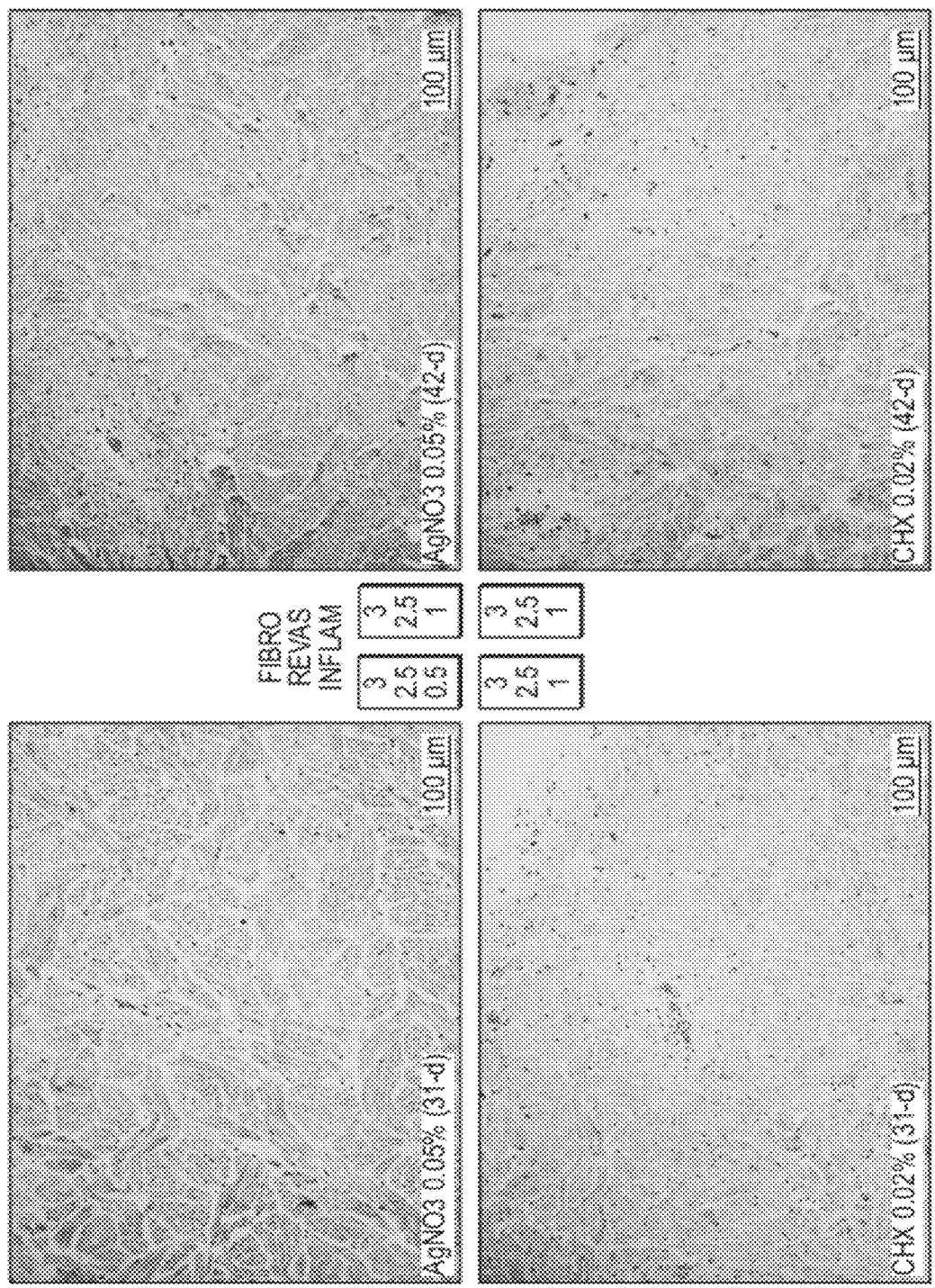

FIG. 2B shows H&E stained 31-day and 42-day sub-dermal explants prepared using silver nitrate and chlorhexidine under 400× magnification. After 31 days, the silver nitrate treated tissue showed significant fibroblast repopulation (Fibro=3), significant revascularization (Revas=2.5), and minimal inflammation (Inflam=0.5). The chlorhexidine treated sample also showed significant fibroblast repopulation and revascularization with minimal inflammation (Fibro=3, Revas=2.5, Inflam=1).

Based on these results, the disclosed method and tissue matrices preserve the functionality of the acellular tissue in vivo by allowing cellular repopulation and revascularization with minimal inflammatory reaction. As demonstrated by FIGS. 1, 2A, and 2B, treatment of the tissue with an anti-microbial agent according to the disclosed method does not interfere with fibroblast repopulation and revascularization when compared to the control tissue. Furthermore, regenerative tissue response is maintained with minimal inflammation compared to the control when the disclosed method is utilized.

EXAMPLE 2

In Vitro Bacterial Growth Inhibition Assay

Tissue matrices with anti-microbial properties were prepared, as described in Example 1, resulting in tissues treated with either 0.25% benzethonium chloride, 0.02% chlorhexidine, 0.1% benzalkonium chloride or 0.001% silver nitrate prepared in water. Control tissues were also prepared using no anti-microbial agent.

Bacteria was prepared for use in an inhibition assay, by inoculating TSB (tryptic soy broth) medium with $E.$ $coli$ or $S.$ $aureus$. The inoculated medium was then incubated at 37° C. with shaking until a population of $0.5-1\times10^9$ cells/ml was reached.

Both the anti-microbial tissues and control tissues were rinsed in saline for two minutes prior to use in the inhibition assay. The tissues were cut into 1.5 cm$^2$ pieces and patted dry using sterile gauze. The tissue pieces were then placed onto TSA (tryptic soy agar) plates.

Both the control and anti-microbial tissues were inoculated individually with 1-2 µl of $0.5-1\times10^9$ cells/ml of the $E.$ $coli$ or $S.$ $aureus$ bacterial solution, so that each piece was seeded with roughly $1\times10^6$ cells. After inoculation, the TSA plates were then incubated at 37° C. for 20 hours. 10 µl of IPTG/X-gal solution was then added to the $E.$ $coli$ inoculated plates only. The X-gal substrate turns blue/green when cleaved by $E.$ $coli$ galactosidase, allowing for easy visualization of bacterial growth. The $E.$ $coli$ plates were then allowed to incubate for an additional 1-2 hours at 37° C.

The effectiveness of the tissue matrices at inhibiting bacterial growth was then determined by visual observation. The growth of $E.$ $coli$ resulted in blue colored colonies while $S.$ $aureus$ growth results in golden colored colonies. Visible growth for both bacteria types was observed for control tissue matrices, i.e., with no anti-microbial. No growth was observed for the tissue matrices treated with benzethonium chloride, chlorhexidine, benzalkonium chloride, or silver nitrate.

The results of the bacterial inhibition assay demonstrate that the disclosed methods and tissue matrices result in which microbial growth is reduced compared to the control tissue without antimicrobial. The results also demonstrate that the disclosed methods and matrices are compatible with a variety of cationic anti-microbial agents and are effective against a variety of bacteria types (e.g., both gram(−) and gram(+) bacteria).

EXAMPLE 3

Evaluation of Anti-Microbial Agent Stability

Figure 3A:
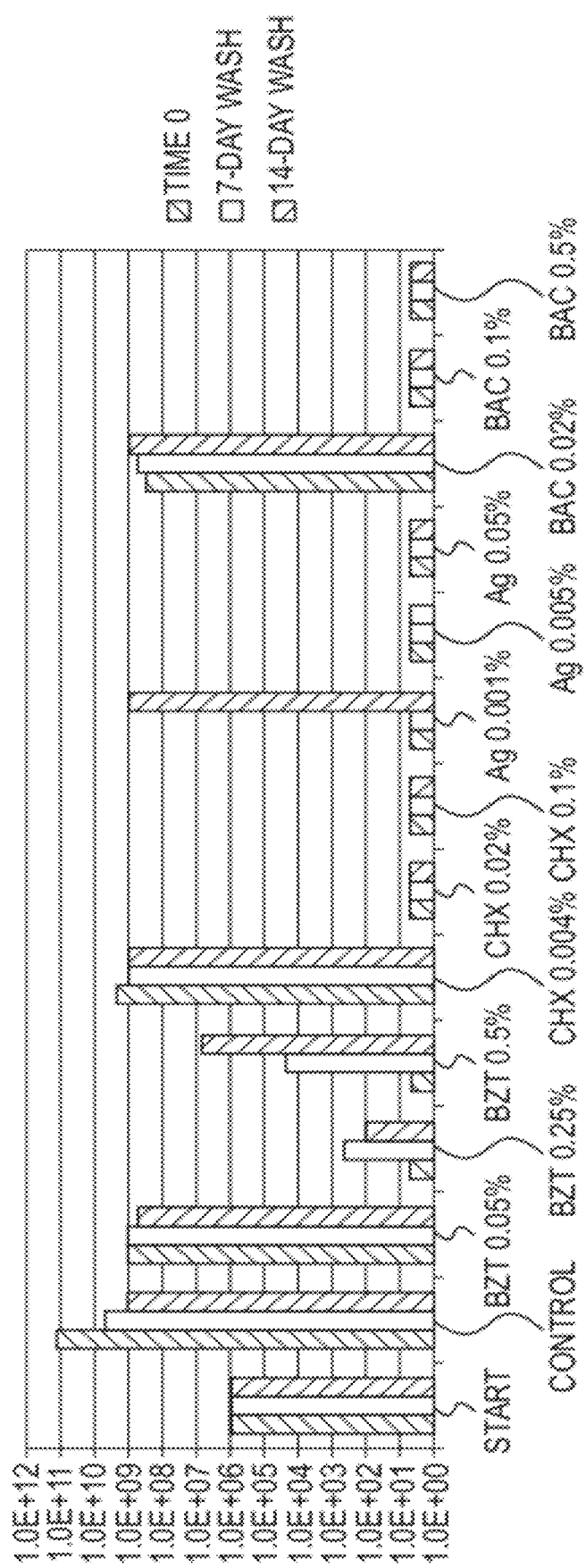
FIGS. 3A and 3B are charts comparing the anti-microbial activity of various tissue matrices as described in Example 3.
Figure 3B:
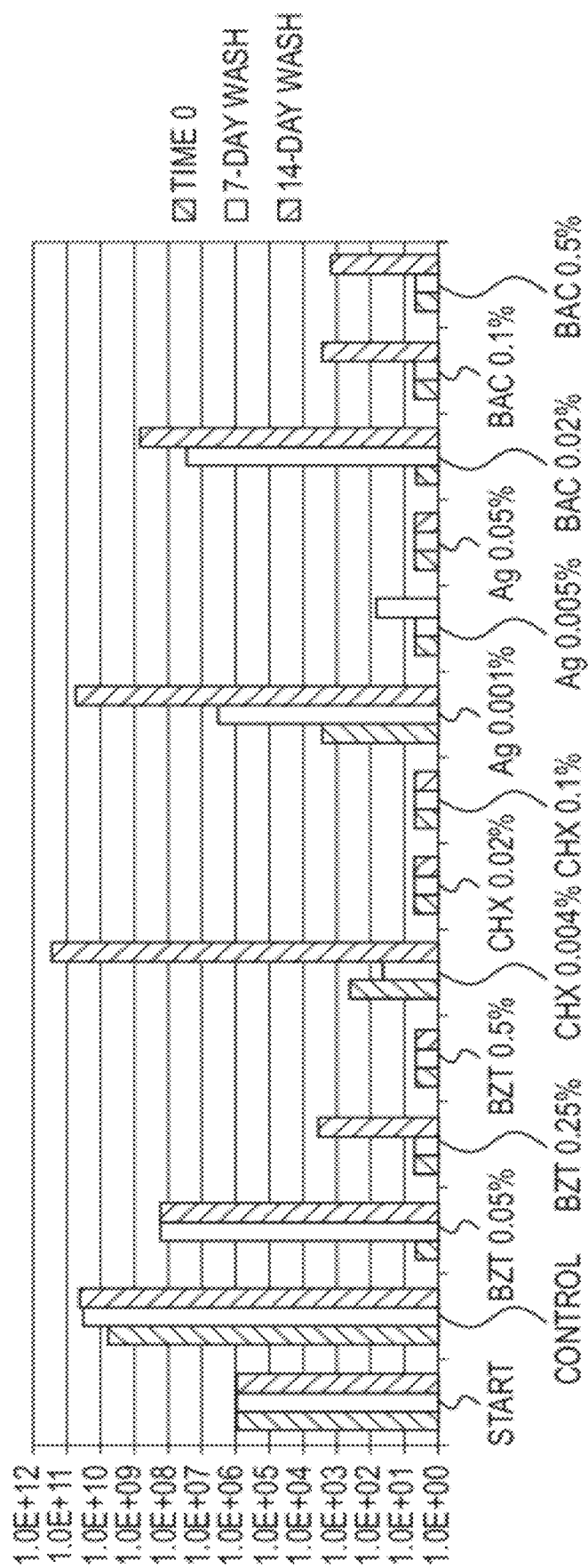

Anti-microbial tissue matrices were prepared, as described in Example 1, resulting in tissues treated with either benzethonium chloride, chlorhexidine, benzalkonium chloride or silver nitrate prepared in water at a range of concentrations (See FIGS. 3A and 3B for concentrations). Control tissues were also prepared using no anti-microbial agent.

The tissues were then washed in PBS solution at 37° C. with shaking and daily changes of PBS for 14 days. At the 7-day and 14-day mark, the anti-microbial activity of the washed tissues was evaluated using the same bacterial growth inhibition assay described in Example 2 for $E.$ $coli$ and $S.$ $aureus$. A drop in anti-microbial activity over time would indicate a lack of stability in the interaction between the tissue matrix and the anti-microbial agent as any bound anti-microbial agent was washed off.

Changes in anti-microbial activity over time were also assessed by measuring colony forming units (CFU) in tissue matrix samples. To measure CFUs, the bacterial growth inhibition assay described in Example 2 was performed on tissue matrices taken at the beginning of the wash period and on tissue matrices that had been washed for 7 or 14 days in PBS as 37° C. with daily changes of PBS. The time 0 samples were not washed. The washed samples were inoculated and cultured, as described in Example 2. After culturing, bacteria was extracted from the tissue matrices by suspending each tissue matrix in 5 ml of PBS and vortexing vigorously for 5 minutes to extract bacteria. The extractant was then serially diluted and plated onto a TSA plate. The TSA plates were then incubated for 24 hours at 37° C. By counting colonies on the plates, the CFU from each tissue piece was calculated.

Results as determined by *E. coli* growth and *S. aureus* growth are presented in FIGS. 3A and 3B, respectively. 0.25% benzethonium chloride, 0.02% and 0.1% chlorhexidine, 0.005% and 0.05% silver nitrate, and 0.1% and 0.5% benzalkonium chloride were effective at inhibiting *E. coli* growth after 14 days. Similar results were observed for *S. aureus*, including the effectiveness of 0.5% benzethonium chloride at inhibiting *S. aureus* growth after 14 days of washing.

FIGS. 3A and 3B demonstrate that the disclosed method and tissue matrices result in the preservation of anti-microbial activity, even when the tissue matrix is washed extensively for 14 days. As shown in this example, the disclosed method and tissue matrices result in the stable interaction between the cationic anti-microbial agent and the acellular tissue matrix.

What is claimed is:

1. An anti-microbial tissue matrix prepared by:
   selecting a collagen-based tissue; and
   contacting the tissue with an aqueous solution containing a cationic anti-microbial agent, wherein the agent is stably bound to a tissue matrix within the collagen-based tissue by passive adsorption in the aqueous solution, and wherein the tissue has been exposed to E-beam radiation.

2. The anti-microbial tissue matrix of claim 1, wherein the aqueous solution is non-denaturing.

3. The anti-microbial tissue matrix of claim 1, wherein the collagen-based tissue is an acellular tissue.

4. The anti-microbial tissue matrix of claim 1, wherein the collagen-based tissue comprises an acellular dermal tissue.

5. The anti-microbial tissue matrix of claim 1, wherein the collagen-based tissue comprises an acellular porcine dermal tissue.

6. The anti-microbial tissue matrix of claim 1, wherein the anti-microbial compound comprises benzethonium chloride, chlorhexidine, benzalkonium chloride, silver nitrate, poly-hexa-methylene biguanide hydrochloride, cationic peptides, chitosan, or quaternary ammonium compounds.

7. The anti-microbial tissue matrix of claim 1, wherein the collagen-based tissue is not cross-linked or denatured during binding of the anti-microbial agent.

8. The anti-microbial tissue matrix of claim 1, wherein the anti-microbial agent is not covalently modified by binding to the collagen-based tissue.

9. The anti-microbial tissue matrix of claim 1, wherein the tissue matrix retains anti-microbial properties for at least two weeks after binding the antimicrobial agent.

10. The anti-microbial tissue matrix of claim 1, prepared by contacting the collagen-based tissue with the aqueous solution containing the cationic anti-microbial agent for at least four hours at room temperature.

11. The anti-microbial tissue matrix of claim 1, wherein the antimicrobial agent remains bound to the tissue matrix when the tissue matrix is placed in a non-denaturing aqueous solution.

12. The anti-microbial tissue matrix of claim 1, wherein the antimicrobial agent remains bound to the tissue matrix when the tissue matrix is placed in PBS.

13. The anti-microbial tissue matrix of claim 1, wherein the bound anti-microbial agent retains greater than 95% of its activity when the tissue matrix is placed in PBS for two weeks at room temperature.

14. The anti-microbial tissue matrix of claim 1, wherein the bound anti-microbial agent retains greater than 75% of its activity when the tissue matrix is placed in PBS for two weeks at room temperature.

15. An anti-microbial tissue matrix comprising:
    a collagen-based tissue; and
    at least one cationic anti-microbial agent that is stably bound to the collagen-based tissue by passive adsorption in an aqueous solution, and wherein the collagen-based tissue has been exposed to E-beam radiation.

16. The anti-microbial tissue matrix of claim 15, wherein binding of the anti-microbial agent to the collagen-based tissue occurs in a non-denaturing aqueous solution.

17. The anti-microbial tissue matrix of claim 15, wherein the collagen-based tissue comprises an acellular dermal tissue.

18. The anti-microbial tissue matrix of claim 15, wherein the collagen-based tissue comprises an acellular porcine dermal tissue.

19. The anti-microbial tissue matrix of claim 15, wherein the anti-microbial compound comprises at least one of benzethonium chloride, chlorhexidine, benzalkonium chloride, silver nitrate, poly-hexa-methylene biguanide hydrochloride, cationic peptides, chitosan, or quaternary ammonium compounds.

20. The anti-microbial tissue matrix of claim 15, wherein the collagen-based tissue is not cross-linked or denatured during binding of the anti-microbial agent.

21. The anti-microbial tissue matrix of claim 15, wherein the anti-microbial agent is not covalently modified by binding to the collagen-based tissue.

22. The anti-microbial tissue matrix of claim 15, wherein the tissue matrix retains anti-microbial properties for at least two weeks after binding the anti-microbial agent.

23. The anti-microbial tissue matrix of claim 15, prepared by contacting the collagen-based tissue with the aqueous solution containing the cationic anti-microbial agent for at least four hours at room temperature.

24. The anti-microbial tissue matrix of claim 15, wherein the antimicrobial agent remains bound to the tissue matrix when the tissue matrix is placed in a non-denaturing aqueous solution.

25. The anti-microbial tissue matrix of claim 15, wherein the antimicrobial agent remains bound to the tissue matrix when the tissue matrix is placed in PBS.

26. The anti-microbial tissue matrix of claim 15, wherein the bound anti-microbial agent retains greater than 95% of its activity when the tissue matrix is placed in PBS for two weeks at room temperature.

27. The anti-microbial tissue matrix of claim 15, wherein the bound anti-microbial agent retains greater than 75% of its activity when the tissue matrix is placed in PBS for two weeks at room temperature.

* * * * *